United States Patent [19]

Schaub et al.

[11] Patent Number: 4,515,782

[45] Date of Patent: May 7, 1985

[54] SUBSTITUTED PHENYL-1-THIO(POLY-O-SULFO)-α(OR β)-D-GLUCOPYRANOSIDES

[75] Inventors: Robert E. Schaub, Upper Saddle River, N.J.; Thomas G. Miner, Chester; Seymour Bernstein, New City, both of N.Y.

[73] Assignee: American Cyanamid Company, Stamford, Conn.

[21] Appl. No.: 527,615

[22] Filed: Aug. 29, 1983

[51] Int. Cl.³ .................... A61K 31/70; C07H 15/00; C07H 15/20
[52] U.S. Cl. ........................................ 514/24; 536/4.1; 536/17.9; 536/17.2; 536/118; 536/18.2; 536/17.5; 536/17.6; 536/122

[58] Field of Search ................ 424/180; 536/118, 122, 536/17.2, 17.5, 17.6, 17.9, 4.1, 18.2

[56] References Cited

U.S. PATENT DOCUMENTS 4,404,195 9/1983 Schaub et al. ...................... 536/118
4,404,365 9/1983 Miner et al. ......................... 536/118

*Primary Examiner*—Johnnie R. Brown
*Attorney, Agent, or Firm*—A. M. Rosenblum

[57] ABSTRACT

Cation salts of substituted phenyl-1-thio(poly-O-sulfo)-α(or β)-D-glucopyranoside, useful as modulators of the complement system, the intermediates thereof and the process of making such intermediates and end products.

19 Claims, No Drawings

SUBSTITUTED PHENYL-1-THIO(POLY-O-SULFO)-α(OR β)-D-GLUCOPYRANOSIDES

BACKGROUND OF THE INVENTION

1. Field of the Invention

The present invention relates to novel cation salts of substituted phenyl-1-thio(poly-O-sulfo)-α(or β)-D-glucopyranoside, to their use as modulators of the complement system of warm-blooded animals, to the intermediates thereof and to the process for the preparation of such intermediates and products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 545, 592, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N. J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819

(1974); J. Med. Chem. 17: 1160 (1974); Biochim. Biophys. Res. Comm. 67: 225 (1975); Ann. N. Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

The sulfated compounds of this invention may be useful in the treatment of ulcers and the like on oral therapy in the form of their aluminum salts.

Also, the non-sulfated intermediate compounds of this invention may be useful as immuno-enhancing agents and potentiators.

SUMMARY OF THE INVENTION

This invention relates to new compounds which are cation salts of substituted phenyl-1-thio(poly-O-sulfo)-α-(or β)-D-glucopyranoside that modulate the complement system, thereby modulating complement activity in body fluids. Moreover, this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

This invention also deals with the novel precursors that act as intermediates in preparing the above-described complement modulating compounds.

DETAILED DESCRIPTION OF THE INVENTION

In accordance with the present invention, there are provided novel compounds represented by the following generic Formula I:

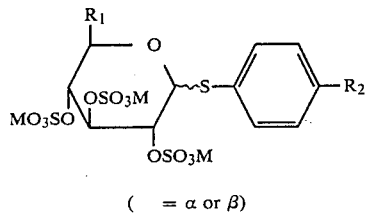

Formula I ( = α or β)

wherein M is a nontoxic pharmaceutically acceptable cation salt, wherein the salt forming moiety is selected from the group consisting of alkali metal, alkaline earth metal, aluminum, zinc, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); $R_1$ is selected from the group consisting of —$COOCH_3$ and —$CH_2OSO_3M$; and $R_2$ is selected from the group consisting of —$OCH_3$, —$NH_2$, —$NHCOCH_3$ and —$NHSO_3M$, which compounds are highly active as complement modulators.

Particularly preferred compounds of Formula I which are of major interest as modulators of the complement system include:

4-aminophenyl 1-thio-(3,4,6-tri-O-sulfo)-β-D-glucopyranosiduronic acid, methyl ester, trisodium salt 4-acetaminophenyl 1-thio-(2,3,4,6-tetra-O-sulfo)-β-D-glucopyranoside tetrasodium salt 4-sulfamoylphenyl 1-thio(2,3,4,6-tetra-O-sulfo)-β-D-glucopyranoside pentasodium salt 4-methoxyphenyl 1-thio(2,3,4,6-tetra-O-sulfo)-β-D-glucopyranoside tetrasodium salt 4-aminophenyl 1-thio-(3,4,6-tri-O-sulfo)-β-D-glucopyranosiduronic acid, methyl ester, tri-triethylammonium salt 4-acetaminophenyl 1-thio-(2,3,4,6-tetra-O-sulfo)-β-D-glucopyranoside tetratriethylammonium salt 4-sulfamoylphenyl 1-thio-(2,3,4,6-tetra-O-sulfo)-β-D-glucopyranoside pentatriethylammonium salt 4-methoxyphenyl 1-thio-(2,3,4,6-tetra-O-sulfo)-β-D-glucopyranoside tetratriethylammonium salt This invention further deals with a method of modulating the complement system in a body fluid, such as blood serum, which comprises subjecting body fluid complement to the action of an effective complement modulating amount of a compound of the above Formula I. Body fluids can include blood, plasma, serum, synovial fluid, cerebrospinal fluid, or pathological accumulations of fluid such as pleural effusion, etc. This invention also concerns a method of modulating the complement system in a warm-blooded animal which comprises administering to said warm-blooded animal an effective complement modulating amount of a compound of the above Formula I.

In addition, this invention is concerned with the precursors in the preparation of the complement modulating compounds of Formula I, shown by the following Formula II:

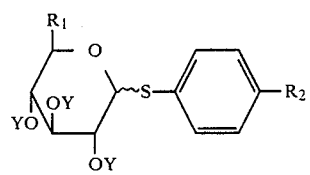

Formula II ( = α or β)

wherein $R_1$ and $R_2$ are as defined in Formula I and Y is selected from the group consisting of —H and —COCH$_3$, which compounds are useful as intermediates for the preparation of the compounds of Formula I.

Specific compounds of Formula II which are of particular interest as intermediates for the production of the compounds of Formula I include the following:

p-aminophenyl 1-thio-(2,3,4,6-tetra-O-acetyl)-β-D-glucopyranoside
p-aminophenyl 1-thio-β-D-glucopyranoside
p-acetamino-1-thio-β-D-glucopyranoside
p-aminophenyl 1-thio-(3,4,6-tri-O-acetyl)-β-D-glucopyranosiduronic acid, methyl ester
p-aminophenyl 1-thio-β-D-glucopyranosiduronic acid, methyl ester
p-methoxyphenyl 1-thio-(2,3,4,6-tetra-O-acetyl)-β-D-glucopyranoside
p-methoxyphenyl 1-thio-β-D-glucopyranoside
p-acetaminophenyl 1-thio-β-D-glucopyranoside Although the compounds of Formula I are shown as being fully sulfated, this invention contemplates partially sulfated products. This invention further contemplates other sugars such as aldo- or keto-hexoses or pentoses or uronic acids.

The compounds of Formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example, inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of Formula II may be useful as immuno-enhancing agents or potentiators.

The compounds of this invention may be prepared according to the following flowchart.

FLOWCHART

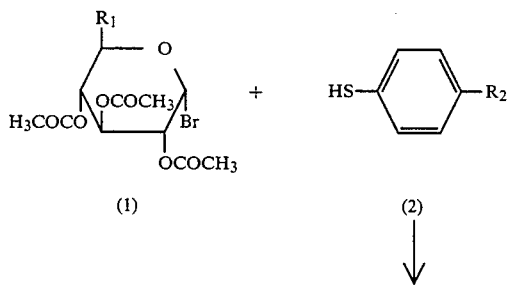

(1) (2)

FLOWCHART

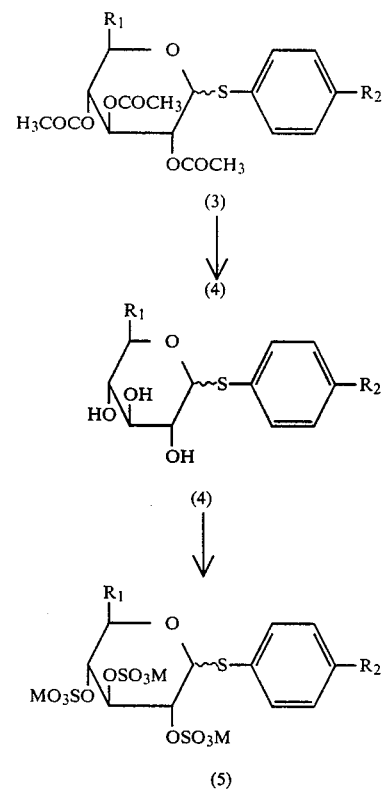

In accordance with the above flowchart an acetobromosugar such as glucose (1), where $R_1$ is as hereinabove described is reacted with a substituted thiophenol (2), where $R_2$ is as described above and sodium hydride in dimethoxyethane at reflux for 8–18 hours, giving a substituted phenyl-1-thio(poly-O-acetyl)-α(or β)-D-glucopyranoside (3) which is then reacted with triethylamine:methanol:water, under an inert atmosphere for several hours, giving a substituted phenyl-1-thio-α(or β)-D-glucopyranoside (4) which is then reacted with a trialkylamine-sulfur trioxide complex in dimethylacetamide at 60°–80° C., under an inert atmosphere for several hours giving (5) where M is N$^+$H(C$_1$-C$_6$alkyl)$_3$ which is then converted to the salt (5) where M is as described above.

It is generally preferred that the respective product of each process step, described hereinabove, is separated and/or isolated prior to its use as starting material for subsequent steps. Separation and isolation can be effected by any suitable purification procedure such as, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salt" refers to those salts of the parent compound which do not significantly or adversely affect the pharmaceutical properties (e.g., toxicity, effectiveness, etc.) of the parent compound. The salt forming moieties of the present invention which are pharmaceutically acceptable include the alkali metals (e.g., sodium, potassium, etc.); alkaline earth metals (e.g., calcium, etc.); aluminum; zinc; ammonia; and substituted ammonia selected from the group consisting of trialkylamine ($C_1$–$C_6$), piperidine, pyrazine, alkanolamine ($C_2$–$C_6$) and cycloalkylamine ($C_3$–$C_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carboxylic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1 p-Aminiphenyl 1-thio-(2,3,4,6-tetra-O-acetyl)-β-D-glycopyranoside

To 700 mg of sodium hydride, under argon, was added 50 ml of dimethoxyethane. The mixture was stirred and 3 g of 4-aminothiophenol in 25 ml of dimethoxyethane were added. After stirring for one hour, a solution of 5 g of acetobromoglucose in 25 ml of dimethoxyethane was added and the mixture was then stirred at reflux temperature for 10 hours. After cooling the crude product was purified by column chromatography, giving 2.8 g of the desired product as buff colored crystals, mp 122°–123° C.

EXAMPLE 2 p-Aminophenyl 1-thio-β-D-glucopyranoside

To a solution of 2.0 g of p-aminophenyl 1-thio(2,3,4,6-tetra-O-acetyl)-β-D-glucopyranoside in a mixture of 50 ml of methanol and 5 ml of acetone was added 4.39 ml of 2N triethylamine in methanol:water (3:6:2). The mixture was allowed to stand 1–24 hours under an argon atmosphere, then taken to dryness in vacuo. The residue was taken up in absolute ethanol, treated with charcoal, filtered and evaporated, giving 1.26 g of the desired product as a glass.

EXAMPLE 3

4-Sulfamoylphenyl 1-thio-(2,3,4,6-tetra-O-sulfo)-β-D-glucopyranoside pentasodium salt To a solution of 1.44 g of p-aminophenyl 1-thio-β-D-glucopyranoside in 20 ml of dimethylacetamide was added 4.29 g of triethylamine-sulfur trioxide complex. The mixture was stirred in an oil bath at 65°–70° C. for 6 hours under an argon atmosphere and then cooled. The mixture was filtered through diatomaceous earth, then diluted with 200 ml of methyl isobutyl ketone and 4 ml of triethylamine, giving the tetratriethylamine salt as a gum. This gum was dissolved in 10 ml of water, 1.3 g of sodium acetate were added, the mixture was filtered and then slowly added to 200 ml of stirred absolute ethanol. Stirring was continued for one hour, then the solid was collected, giving 2.69 g of the desired product.

EXAMPLE 4 p-Acetaminophenyl 1-thio-β-D-glucopyranoside

To a solution of 1.77 g of p-aminophenyl-1-thio-β-D-glucopyranoside in 10 ml of water was added 0.9 ml of acetic anhydride. The solution was shaken for 7 minutes, then taken to dryness and evaporated with toluene to a residue. This residue was crystallized from ethyl acetate giving 2.0 g of the desired product, mp. 160°–163° C.

EXAMPLE 5

4-Acetaminophenyl 1-thio-(2,3,4,6-tetra-O-sulfo)-β-D-glucopyranoside tetrasodium salt A 10 g portion of triethylamine-sulfur trioxide complex was dissolved in 45 ml of dimethylacetamide. A 10 g portion of 4 Å molecular sieves was added and the mixture was warmed to 60° C. A 1.8 g portion of p-acetaminophenyl 1-thio-β-D-glucopyranoside was added and the mixture was heated at 60°–65° C. under argon for 42 hours. The mixture was filtered into 650 ml of acetone producing a gum which was the tetratriethylamine salt. This gum was dissolved in a solution of 2.2 g of sodium acetate in 15 ml of water, stirred for 12 minutes, filtered and the filtrate added in a thin stream to 1200 ml of absolute ethanol. The resulting solid was collected giving 2.47 g of the desired product, mp 130°–135° C. (dec.).

EXAMPLE 6 p-Aminophenyl 1-thio-(3,4,6-tri-O-acetyl)-β-D-glucopyranosiduronic acid, methyl ester To a mixture of 700 mg of 50% sodium hydride in 50 ml of dry dimethoxyethane, stirred under argon, was added dropwise a solution of 3 g of 4-aminothiophenol in 25 ml of dimethoxyethane. This mixture was stirred for 2 hours, then there was added a solution of 4.8 g of methyl acetobromoglucuronate in 25 ml of dimethoxyethane. This mixture was stirred overnight under argon and the crude product was collected, purified by chromatography and crystallized from ether, giving 2.41 g of the desired product, as off-white crystals, mp 128°–130° C.

EXAMPLE 7 p-Aminophenyl 1-thio-$\beta$-D-glucopyranosiduronic acid, methyl ester

4-Aminophenyl 1-thio-(3,4,6-tri-O-acetyl)-$\beta$-D-glucopyranosiduronic acid, methyl ester may be treated as described in Example 2 to derive the desired product.

EXAMPLE 8

4-Aminophenyl 1-thio-(3,4,6-tri-O-sulfo)-$\beta$-D-glucopyranosiduronic acid, methyl ester, trisodium salt 4-Aminophenyl 1-thio-$\beta$-D-glucopyranosiduronic acid, methyl ester may be treated as described in Example 3 to derive first the tri-triethylammonium derivative and then the desired trisodium derivative.

EXAMPLE 9 p-Methoxyphenyl 1-thio-(2,3,4,6-tetra-O-acetyl)-$\beta$-D-glucopyranoside

To a slurry of 0.6 g of 50% sodium hydride in 50 ml of tetrahydrofuran was added 2.8 g of p-methoxythiophenol. After ½ hour a solution of acetobromoglucose in tetrahydrofuran was added followed by 5 ml of hexamethylphosphoramide. The mixture was stirred for 3 hours, filtered and the filtrate extracted with 50 ml of 5N sodium hydroxide and then 50 ml of water. The organic layer was dried and concentrated to an oil. The oil was purified by chromatography, giving 1.0 g of the desired product, mp 99°-101° C.

EXAMPLE 10 p-Methoxyphenyl 1-thio-$\beta$-D-glucopyranoside

To a chilled (−5° C.) solution of 4.0 g of p-methoxyphenyl 1-thio-(2,3,4,6-tetra-O-acetyl)-$\beta$-D-glucopyranoside in 60 ml of methanol was added 40 ml of a solution of 2N triethylamine:methanol:water (3:6:2). The solution was refrigerated at +5° C. for 16 hours then concentrated in vacuo, giving 2.6 g of the desired product.

EXAMPLE 11

4-Methoxyphenyl 1-thio-(2,3,4,6-tetra-O-sulfo)-$\beta$-D-glucopyranoside tetrasodium salt To a solution of 1.1 g of p-methoxyphenyl 1-thio-$\beta$-D-glucopyranoside in 50 ml of dry acetone was added 3.9 g of triethylamine-sulfur trioxide complex and 2 g of 3 Å molecular sieves. The reaction was heated at reflux for several hours, then cooled, diluted with water and filtered. The filtered solution was concentrated to a syrup which was purified by chromatography, giving the tetratriethylamine derivative, which was then converted to the tetrasodium derivative, giving 0.9 g of the product.

EXAMPLE 12

Preparation of Compressed Tablet

| Ingredient | mg./Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 13

Preparation of Compressed Tablet—Sustained Action

| Ingredient | mg./Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement modulator plus aluminum sulfate yields aluminum complement modulator. Complement modulator content in aluminum lake ranges from 5–30%.

EXAMPLE 14

Preparation of Hard Shell Capsule

| Ingredient | mg./Capsule |
| --- | --- |
| Active Compound | 0.5–500 |
| Lactose, Spray Dried | qs |
| Magnesium Stearate | 1–10 |

EXAMPLE 15

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 16

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 17

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |

-continued

| Ingredient | % W/V |
|---|---|
| Purified Water qs ad | 100.0 |

EXAMPLE 18

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 19

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 20

Preparation of Intra-Articular Product

| Ingredient | Amount |
|---|---|
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 21

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 22

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs | 100 |

EXAMPLE 23

Preparation of Dental Ointment

| Ingredient | % W/W |
|---|---|
| Active Compound | 0.05–5 |
| Petrolatum, White USP qs | 100 |

EXAMPLE 24

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 25

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 26

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 27

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 28

Preparation of Buccal Tablet

| Ingredient | g./Tablet |
|---|---|
| Active Ingredient | 0.00325 |
| 6 × Sugar | 0.29060 |
| Acacia | 0.01453 |
| Soluble Starch | 0.01453 |

-continued

| Ingredient | g./Tablet |
| --- | --- |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 29

Preparation of Lozenge

| Ingredient | g./Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into $\tfrac{5}{8}''$ flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodonatlly for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form", as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement modulating activity of compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; and (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9. The results of Test Codes 026 and 035 appear in Table I showing that the principal compounds of the invention possess highly significant complement modulating activity in warm-blooded animals.

TABLE I

| Compound | Biological Activities | |
|---|---|---|
| | In vitro Activity | |
| | C-1 026* Wells | C-Late 035* Wells |
| 4-Sulfamoylphenyl 1-thio-(2,3,4,6-tetra-O—sulfo)-β-D-glucopyranoside pentasodium salt | 5** | |
| 4-Acetaminophenyl 1-thio-(2,3,4,6-tetra-O—sulfo)-β-D-glucopyranoside tetrasodium salt | 4 | 2 |
| 4-Methoxyphenyl 1-thio-(2,3,4,6-tetra-O—sulfo)-β-D-glucopyranoside tetrasodium salt | 1 | |

*Tests identified by code herein. For a discussion of the tests, see "Systematic Discovery & Evaluation of Complement Inhibitors," N. Bauman et at., Immunopharmacology 3: 317–24 (1981).
**Activity in wells, a serial dilution assay; higher well number indicates higher activity. The serial dilutions are two-fold.

We claim:

1. A compound selected from those of the formula:

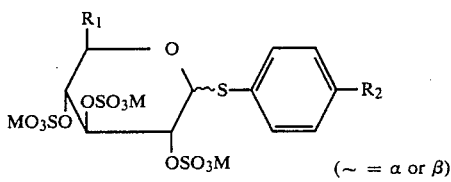

($\sim$ = $\alpha$ or $\beta$)

wherein M is a nontoxic pharmaceutically acceptable cation salt, wherein the salt forming moiety is selected from the group consisting of alkali metal, alkaline earth metal, aluminum, zinc, ammonia and substituted ammonia selected from the group consisting of trialkylamine ($C_1$-$C_6$), piperidine, pyrazine, alkanolamine ($C_2$-$C_6$) and cycloalkylamine ($C_3$-$C_6$); $R_1$ is selected from the group consisting of —COOCH$_3$ and —CH$_2$OSO$_3$M; and $R_2$ is selected from the group consisting of —OCH$_3$, —NH$_2$, —NHCOCH$_3$ and —NHSO$_3$M.

2. The compound according to claim 1, 4-aminophenyl 1-thio-(3,4,6-tri-O-sulfo)-β-D-glucopyranosiduronic acid, methyl ester, trisodium salt, having the structure

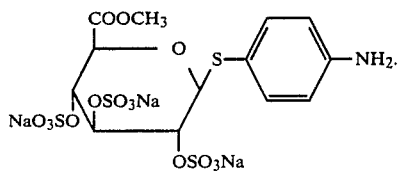

3. The compound according to claim 1, 4-acetaminophenyl 1-thio-(2,3,4,6-tetra-O-sulfo)-β-D-glucopyranoside tetrasodium salt, having the structure

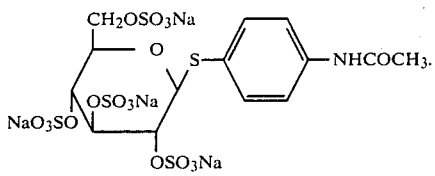

4. The compound according to claim 1, 4-sulfamoylphenyl 1-thio-(2,3,4,6-tetra-O-sulfo)-β-D-glucopyranoside pentasodium salt, having the structure

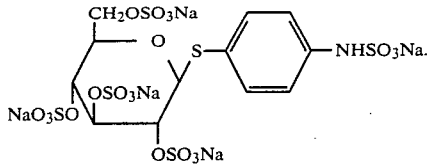

5. The compound according to claim 1, 4-methoxyphenyl 1-thio-(2,3,4,6-tetra-O-sulfo)-β-D-glucopyranoside tetrasodium salt, having the structure

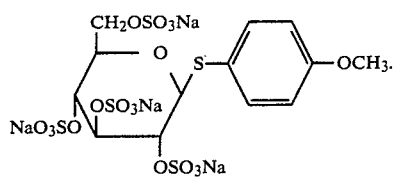

6. The compound according to claim 1, 4-sulfamoylphenyl 1-thio-(2,3,4,6-tetra-O-sulfo)-β-D-glucopyranoside pentatriethylammonium salt, having the structure

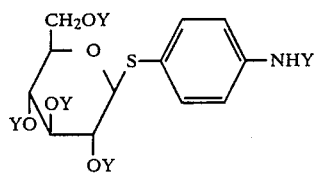

wherein Y is SO$^-_3$.NH$^+$($C_2H_5$)$_3$.

7. The compound according to claim 1, 4-acetaminophenyl 1-thio-(2,3,4,6-tetra-O-sulfo)-β-D-glucopyranoside tetratriethylammonium salt, having the structure

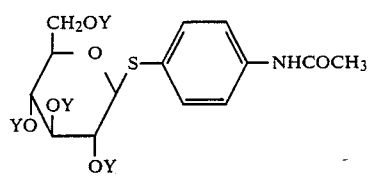

where Y is SO$^-_3$.NH$^+$($C_2H_5$)$_3$.

8. The compound according to claim 1, 4-aminophenyl 1-thio-(3,4,6-tri-O-sulfo)-β-D-glucopyranosiduronic acid, methyl ester, tri-triethylammonium salt, having the structure

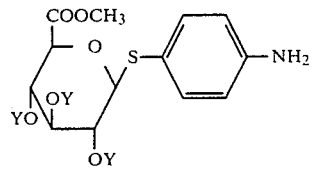

where Y is SO$^-_3$.NH$^+$($C_2H_5$)$_3$.

9. The compound according to claim 1, 4-methoxyphenyl 1-thio-(2,3,4,6-tetra-O-sulfo)-β-D- glucopyranoside tetratriethylammonium salt, having the structure

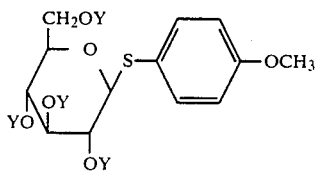

where Y is $SO^-_3 \cdot NH^+(C_2H_5)_3$.

10. A compound selected from those of the formula:

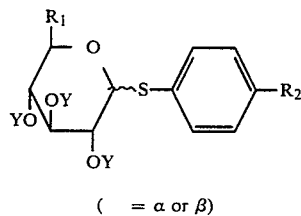

( ∼ = α or β )

wherein Y is selected from the group consisting of —H and —COCH₃; R₁ is selected from the group consisting of —COOCH₃ and —CH₂OY; and R₂ is selected from the group consisting of —OCH₃, —NH₂ and —NHCOCH₃.

11. The compound according to claim 10, p-aminophenyl 1-thio-(2,3,4,6-tetra-O-acetyl)-β-D-glucopyranoside, having the structure

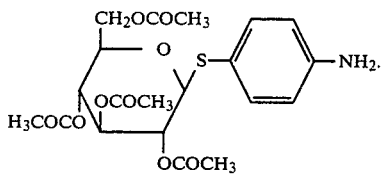

12. The compound according to claim 10, p-aminophenyl 1-thio-β-D-glucopyranoside, having the structure

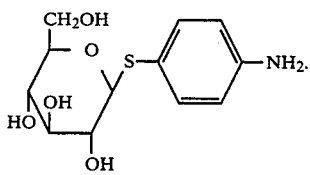

13. The compound according to claim 10, p-acetaminophenyl 1-thio-β-D-glucopyranoside, having the structure

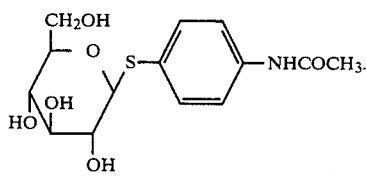

14. The compound according to claim 10, p-aminophenyl 1-thio-(3,4,6-tri-O-acetyl)-β-D-glucopyranosiduronic acid, methyl ester, having the structure

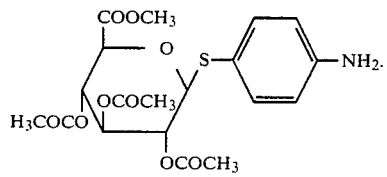

15. The compound according to claim 10, p-aminophenyl 1-thio-β-D-glucopyranosiduronic acid, methyl ester having the structure

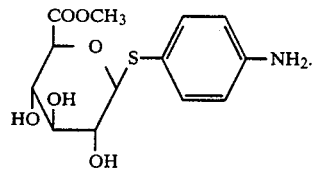

16. The compound according to claim 10, p-methoxyphenyl 1-thio-(2,3,4,6-tetra-O-acetyl)-β-D-glucopyranoside, having the structure

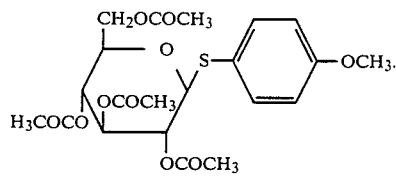

17. The compound according to claim 10, p-methoxyphenyl 1-thio-β-D-glucopyranoside, having the structure

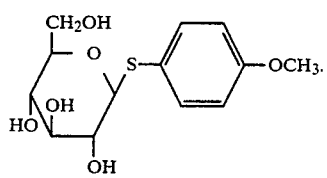

18. A method of modulating the complement system in a body fluid which comprises subjecting said body fluid to the action of an effective complement modulating amount of a pharmaceutically acceptable compound of the formula:

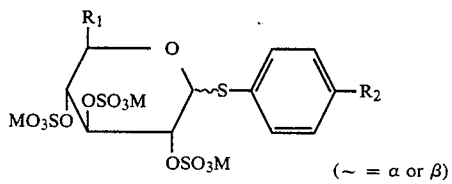

( ∼ = α or β )

wherein M is a nontoxic pharmaceutically acceptable cation salt, wherein the salt forming moiety is selected from the group consisting of alkali metal, alkaline earth metal, aluminum, zinc, ammonia and substituted ammonia selected from the group consisting of trialkylamine (C₁–C₆), piperidine, pyrazine, alkanolamine (C₂–C₆)

and cycloalkylamine ($C_3$–$C_6$); $R_1$ is selected from the group consisting of —COOCH$_3$ and —CH$_2$OSO$_3$M; and $R_2$ is selected from the group consisting of —OCH$_3$, —NH$_2$, —NHCOCH$_3$ and —NHSO$_3$M.

19. A method of modulating the complement system in a warm-blooded animal which comprises administering to said animal an effective complement modulating amount of a pharmaceutically acceptable compound of the formula:

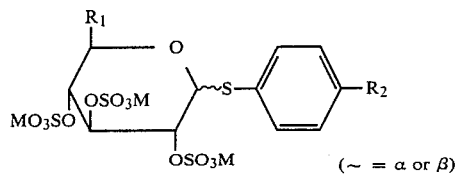

($\sim$ = α or β)

wherein M is a nontoxic pharmaceutically acceptable cation salt, wherein the salt forming moiety is selected from the group consisting of alkali metal, alkaline earth metal, aluminum, zinc, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); $R_1$ is selected from the group consisting of —COOCH$_3$ and —CH$_2$OSO$_3$M; and $R_2$ is selected from the group consisting of —OCH$_3$, —NH$_2$, —NHCOCH$_3$ and —NHSO$_3$M.

* * * * *